United States Patent
Li et al.

(10) Patent No.: US 12,110,315 B1
(45) Date of Patent: Oct. 8, 2024

(54) FISH-DERIVED PEPTIDOGLYCAN RECOGNITION PROTEIN MUTANT AND APPLICATION THEREOF

(71) Applicant: OCEAN UNIVERSITY OF CHINA, Qingdao (CN)

(72) Inventors: Qingfei Li, Qingdao (CN); Qinghui Ai, Qingdao (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 18/607,763

(22) Filed: Mar. 18, 2024

(30) Foreign Application Priority Data

Mar. 21, 2023 (CN) .......................... 202310275338.7

(51) Int. Cl.
  *A61P 37/04*  (2006.01)
  *A61K 38/00*  (2006.01)
  *A61P 31/04*  (2006.01)
  *C07K 14/46*  (2006.01)

(52) U.S. Cl.
  CPC ............. *C07K 14/461* (2013.01); *A61P 31/04* (2018.01); *A61P 37/04* (2018.01); *A61K 38/00* (2013.01)

(58) Field of Classification Search
  CPC .................................. A61K 38/00; A61P 31/04
  See application file for complete search history.

(56) References Cited

FOREIGN PATENT DOCUMENTS

KR  2020014975 A  * 2/2020  ........... A23K 20/147

OTHER PUBLICATIONS

English translation of KR-20200014975-A obtained from PE2E on May 31, 2024 (Year: 2024).*
Li et al., "Molecular identification of peptidoglycan recognition protein 5 and its functional characterization in innate immunity of large yellow croaker, Larimichthys crocea", Developmental and Comparative Immunology, 124, 10 pages, available online May 31, 2021 (Year: 2021).*

* cited by examiner

*Primary Examiner* — Nicole P Babson
*Assistant Examiner* — John P Nguyen
(74) *Attorney, Agent, or Firm* — Jeenam Park

(57) ABSTRACT

A fish-derived peptidoglycan recognition protein mutant and an application thereof are provided. An amino acid sequence of the mutant is shown in SEQ ID NO. 1, a nucleotide sequence of the mutant is shown in SEQ ID NO. 2. The present disclosure provides the preparation method for the mutant with a broad-spectrum antibacterial activity and robust inhibitory effects on both Gram-positive and Gram-negative bacteria. Compared with the wild-type LcPGRP5 protein, the mutant protein demonstrates a stronger ability to inhibit the activity against *Staphylococcus aureus* and enhance the phagocytic ability of fish macrophages.

1 Claim, 4 Drawing Sheets

Specification includes a Sequence Listing.

SEQUENCE LISTING

```
Sequence total quantity: 6
SEQ ID NO: 1           moltype = AA  length = 167
FEATURE                Location/Qualifiers
source                 1..167
```

-continued

```
                         mol_type = protein
                         organism = synthetic construct
SEQUENCE: 1
MDQKVNIVSR  VQWGAAAPRK  KETLKDCAQR  VVIHHTALPK  CTGMKECVDR  LVSIQRAHMT   60
ERRFDDIGYN  FLVGGDGTVY  EGRGWGVVGA  HTKGHNHDSL  GIAFMGNYNS  DAPSTEALSA  120
VKQLLQSGVS  QGFLQPEFVL  FGARDLGSTQ  CPGDKLYAAL  PQLRGTT                 167

SEQ ID NO: 2             moltype = DNA   length = 504
FEATURE                  Location/Qualifiers
source                   1..504
                         mol_type = other DNA
                         organism = synthetic construct
SEQUENCE: 2
atggatcaga  aagttaacat  cgttagtcgc  gttcagtggg  gcgcagcagc  accgcgtaaa   60
aaagaaaccc  tgaaagattg  cgcacagcgc  gttgttattc  atcataccgc  actgccgaaa  120
tgtaccggca  tgaaagaatg  tgttgatcgt  ctggtgagca  ttcagcgcgc  ccacatgacc  180
gaacgtcgtt  ttgatgatat  tggttataat  ttcctggtgg  gcggtgatgg  taccgtgtat  240
gaaggtcgtg  gttggggtgt  tgttggcgca  cataccaaag  gccataatca  tgatagtctg  300
ggcattgcct  ttatgggcaa  ttataatagt  gatgccccga  gtaccgaagc  cctgagcgca  360
gttaaacagc  tgctgcagag  tggcgtgagt  cagggttttc  tgcagccgga  atttgtgctg  420
tttggtgcac  gcgatctggg  tagtacccag  tgtccgggtg  ataaactgta  tgcagccctg  480
ccgcagctgc  gtggcaccac  ataa                                            504

SEQ ID NO: 3             moltype = DNA   length = 22
FEATURE                  Location/Qualifiers
source                   1..22
                         mol_type = other DNA
                         organism = synthetic construct
SEQUENCE: 3
atggaccaaa  aagtgaacat  tg                                               22

SEQ ID NO: 4             moltype = DNA   length = 24
FEATURE                  Location/Qualifiers
source                   1..24
                         mol_type = other DNA
                         organism = synthetic construct
SEQUENCE: 4
ttatgtggta  cccctcagtt  gtgg                                             24

SEQ ID NO: 5             moltype = DNA   length = 26
FEATURE                  Location/Qualifiers
source                   1..26
                         mol_type = other DNA
                         organism = synthetic construct
SEQUENCE: 5
caccatggac  caaaaagtga  acattg                                           26

SEQ ID NO: 6             moltype = DNA   length = 24
FEATURE                  Location/Qualifiers
source                   1..24
                         mol_type = other DNA
                         organism = synthetic construct
SEQUENCE: 6
ttatgtggta  cccctcagtt  gtgg                                             24
```

FISH-DERIVED PEPTIDOGLYCAN RECOGNITION PROTEIN MUTANT AND APPLICATION THEREOF

CROSS-REFERENCE TO RELATED APPLICATIONS

This application claims priority to Chinese Patent Application No. 202310275338.7, filed on Mar. 21, 2023, which is hereby incorporated by reference in its entirety.

TECHNICAL FIELD

The present disclosure relates to the field of biology technologies, and in particular, to a preparation method and application of a novel fish derived peptidoglycan recognition protein mutant.

SEQUENCE LISTING

The present application contains a sequence listing which has been filed electronically in xml format and is hereby incorporated by reference in its entirety. Besides, a copy of the sequence listing in XML file is submitted later, the XML copy was created on Mar. 5, 2024, was named "FISH-DERIVED PEPTIDOGLYCAN RECOGNITION PROTEIN MUTANT AND APPLICATION THEREOF-Sequence Listing" and is 7,153 bytes in size.

BACKGROUND

As a lower vertebrate, bony fish have a well-developed innate immune system that can recognize the invasion and infection of bacteria and viruses through pattern recognition receptors (PRRs), mediating immune cells to exert immune regulatory functions. Research has shown that peptidoglycan recognition protein (PGRP) with multiple physiological functions play a prominent role in an innate immune response against microbial infections.

PGRPs are evolutionarily conserved PRRs from insects to mammals with a shared 160 amino acid PGRP domain. A PGRP family consisting of four genes has been found in mammals, while insects have more (for example, 13 genes encoding 19 proteins in *Drosophila*). According to published reports, there are three types of PGRP genes in fish, named PGRP2, PGRP5 (PGRP-SC), and PGRP6, respectively.

Studies in insects and mammals have shown that PGRP controls the level of symbiotic bacteria in mammalian and insect bodies and resists infections from other bacteria through a direct effect (bactericidal and antibacterial activity) and an indirect effect (inducing antimicrobial peptides, regulating inflammation and immune responses). Similarly, studies in fish have shown that PGRP plays an important role in immune regulatory functions such as pathogen recognition, microbial aggregation, induction of apoptosis, and promotion of phagocytosis. In addition, fish PGRP is also an amidase that can hydrolyze the amide bond between N-acetyl wall acid and alanine in peptidoglycan molecules, causing the peptidoglycan molecules to lose activity and achieve a goal of killing bacteria. Considerable evidence has exhibited that PGRP can also interact with peptidoglycans on the surface of microorganisms, activate downstream cascade signal transduction, and activate a production of inflammatory mediators, therefore, it is a key immune effector molecule for clearing bacteria.

In recent decades, outbreaks of infectious diseases caused by pathogenic bacteria such as *Vibrio harveyi*, *Vibrio algi-nolyticus*, Filamentous Nocardia, and Pseudomonas have caused serious economic losses, thereby posing a huge challenge to a sustainable development of fish farming. It is imperative to source a solution to this bottleneck, find a key target for regulating fish immunity, and develop a precise regulatory strategy to improve the immunity and health of aquaculture fish, which is of great significance for ensuring the sustainable development of the aquaculture industry. Existing studies have shown that LPS or inactivated bacterial vaccines can significantly increase the expression of PGRP5 in large yellow croaker, indicating that PGRP5 plays an important role in the immune process induced by bacteria. This provides an important theoretical basis for developing regulatory strategy through PGRPs to promote health management in aquaculture practices. Moreover, there have been reports concerning producing recombinant fish peptidoglycan recognition proteins through a genetic engineering method, but there are still issues such as unclear mechanisms of function, low biological activity, and limited application scenarios.

SUMMARY

The purpose of the present disclosure is to provide a fish derived peptidoglycan recognition protein mutant, a preparation method, and an application thereof, analyze its active function, and apply it in the field of nutritional immunity.

The present disclosure is implemented through the following technical solutions.

A fish derived peptidoglycan recognition protein mutant, amino acid sequence of the mutant is shown in SEQ ID NO. 1, a nucleotide sequence of the fish derived peptidoglycan recognition protein mutant is shown in SEQ ID NO. 2.

```
SEQ ID NO. 1:
MDQKVNIVSRVQWGAAAPRKKETLKDCAQRVVIHHTALPKCTGMKECVDR

LVSIQRAHMTERRFDDIGYNFLVGGDGTVYEGRGWGVVGAHTKGHNHDSL

GIAFMGNYNSDAPSTEALSAVKQLLQSGVSQGFLQPEFVLFGARDLGSTQ

CPGDKLYAALPQLRGTT;

SEQ ID NO. 2:
atggatcagaaagttaacatcgttagtcgcgttcagtggggcgcagcagc accgcgtaaaaagaaaccctgaaagattgcgcacagcgcgttgttattc atcataccgcactgccgaaatgtaccggcatgaaagaatgtgttgatcgt ctggtgagcattcagcgcgcccacatgaccgaacgtcgttttgatgatat tggttataatttcctggtgggcggtgatggtaccgtgtatgaaggtcgtg gttggggtgttgttggcgcacataccaaaggccataatcatgatagtctg ggcattgcctttatgggcaattataatagtgatgccccgagtaccgaagc cctgagcgcagttaaacagctgctgcagagtggcgtgagtcagggttttc tgcagccggaatttgtgctgtttggtgcacgcgatctgggtagtacccag tgtccgggtgataaactgtatgcagccctgccgcagctgcgtggcaccac ataa.
```

The present disclosure further provides a method for preparing a mutant of fish-derived peptidoglycan recognition protein. The preparation method includes: amplifying a target fragment by PCR reaction using the mutant gene as the template to obtain a target gene with a connector; connecting the amplified PCR product to a prokaryotic expression system vector pET-PDE1 through homologous recombination; introducing the recombinant mutant plasmid into an *Escherichia coli* expression system; screening and obtaining highly efficient expression strains; inoculating them in a culture medium with added antibiotics; inducing the expression of recombinant fusion protein in bacteria by adding IPTG; continuing to culture and collecting bacterial precipitates by centrifugation; lysing bacterial cells and collecting inclusion bodies; after washing, denaturation, dissolution, dialysis, and renaturation; purifying a supernatant containing recombinant protein labeled with histidine using affinity chromatography.

The present disclosure further provides an application of the fish-derived peptidoglycan recognition protein mutant in a preparation of an antibacterial agent.

The present disclosure additionally provides an application of the fish-derived peptidoglycan recognition protein mutant in the development of an immune enhancer or a feed additive for aquatic animals.

The beneficial effects of the present disclosure compared to prior article are as follows:
 a novel peptidoglycan recognition protein mutant prepared by the present disclosure is engineered with targeted mutagenesis towards specific amino acids of wild peptidoglycan recognition proteins for, thereby enhancing the biological activity.

The novel peptidoglycan recognition protein mutant gene in the present disclosure has been processed with codon optimization, which facilitates the recognition and expression of codons in *Escherichia coli* cells, thereby improving the efficiency of prokaryotic expression of recombinant proteins.

The present disclosure introduces a recombinant plasmid of peptidoglycan recognition protein mutant into an *Escherichia coli* cells expression system. Through screening, highly efficient expression strains are identified and obtained. After induction, separation, and purification, highly active recombinant mutant proteins can be produced. The production process has been meticulously optimized to enable potential large-scale production.

The peptidoglycan recognition protein mutant prepared in the present disclosure has robust amidase activity, can degrade both L-type and D-type peptidoglycans, with a particular efficacy against L-type peptidoglycans from Gram-positive bacteria.

The peptidoglycan recognition protein mutant prepared in the present disclosure demonstrates broad-spectrum antibacterial activity and potent inhibitory effects against both Gram-positive and Gram-negative bacteria.

The peptidoglycan recognition protein mutant prepared in the present disclosure showcases enhanced antibacterial activity. Compared with a wild-type LcPGRP5 protein, the mutant protein has stronger inhibitory activity against *Staphylococcus aureus*.

The peptidoglycan recognition protein mutant prepared in the present disclosure can enhance the phagocytic activity of macrophages. Fish macrophages incubated with added recombinant mutant protein showed a notably increased phagocytic rate against *Staphylococcus aureus* (70.7%), which was significantly higher than that of a treatment group adding with wild-type rLcPGRP5 (57.2%) and the control group (48%).

DESCRIPTION OF EMBODIMENTS

Figure 1:
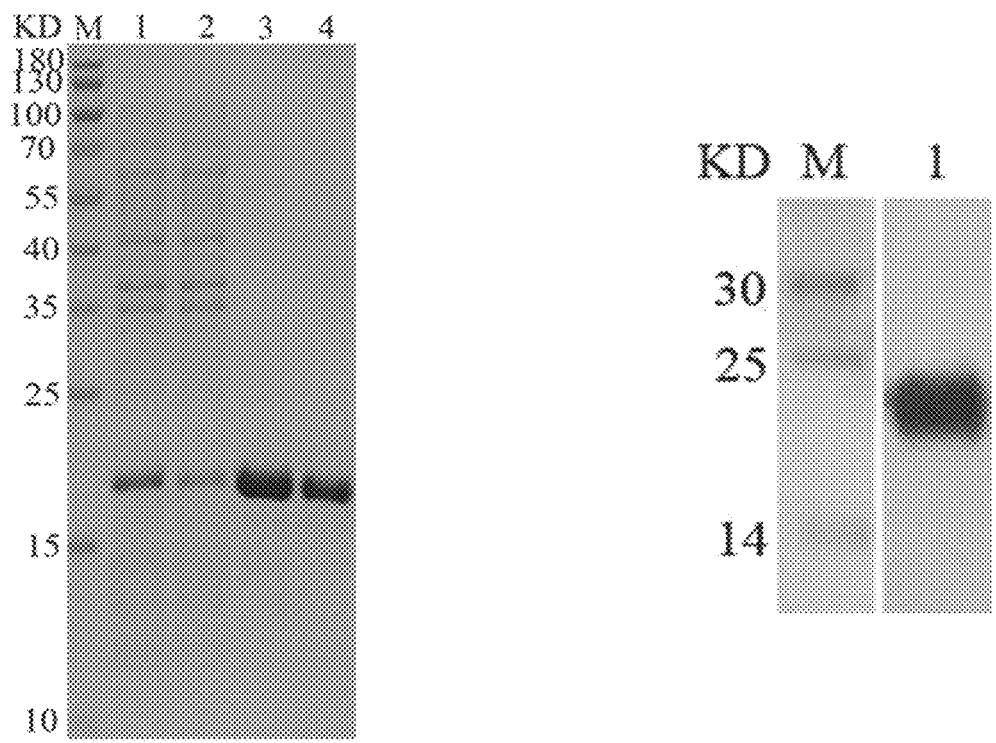
FIG. 1 SDS-PAGE analysis graph and a Western blot identification analysis graph of a purified mutant protein indicated by the arrows.

The present disclosure relates to a preparation method and application of a novel fish-derived peptidoglycan recognition protein mutant. Firstly, wild LcPGRP5 gene was cloned, a codon of prokaryotic expression was optimized. Mutation was performed on a specific amino acid within the gene; full-length of mutated gene was artificially synthesized. The mutant gene was subsequently ligated into a prokaryotic expression system vector pET-PDE1 using directed topoisomerase cloning technology. The recombinant mutant plasmid was induced into an *Escherichia coli* expression system, then highly efficient expression strains were screened and obtained. The expression of recombinant fusion proteins was induced in bacteria, and mutated peptidoglycan recognition proteins were obtained after lysis and purification.

The specific steps of the method are as follows:
1. Firstly, a primer was designed with reference to LcPGRP5 sequence reported in the GenBank (GenBank NO.: MW468048.1) (the specific primers were: F: ATGGACCAAAAAGTGAACATTG (SEQ ID NO.: 3); R: TTATGTGGTACCCCTCAGTTGTGG (SEQ ID NO.: 4)). Large yellow croaker cDNA was used as a template, PRIMERSTAR MAX enzyme provided by TAKARA Company was used to conduct a PCR amplification reaction at 98° C. for 10 s, 55° C. for 15 s, and 72° C. for 1 min for a total of 35 cycles. PCR products were separated by 1.2% agarose gel electrophoresis, a gel band with the target fragment was extracted according to the instruction of DNA gel extraction kit (Sango Biotech, China). Extracted PCR product was cloned to the pEASY-BLUNT vector (TransGen Biotech Co., Ltd., China) followed by transformation of resultant plasmid into competent *E. coli* cells
for overnight culture. and positive monoclonal colonies were selected for sequencing and validation. After bacteria culture and plasmid extraction, plasmids with the wild-type LCPGRP5 gene were obtained.
2. Codon of LcPGRP5 gene was optimized for prokaryotic expression and mutation was performed on the target amino acid codon to acquire the mutant gene. Forward and reverse primers with an adaptor were designed (F: CACCATGGACCAAAAAGTGAACATTG (SEQ ID NO.: 5); R: TTATGTGGTACCCCTCAGTTGTGG (SEQ ID NO.: 6)), the target gene with an adaptor was amplified using a codon-optimized mutant gene template which was artificially synthesized. Directed topoisomerase cloning technology was used to clone the amplified PCR products into the expression vector pET-PDE1. Reaction system (10 µL) is displayed as follows: 0.5-8 purified PCR product, vector 1 µL, 1 µL 10× Enhancer, DEPC water was added to fill the volume up to 10 µL. After placement for 5 minutes at room temperature. A prokaryotic expression vector containing 6 histidine residues for the expression product was constructed.
3. Plasmids were transformed using calcium chloride method, and positive transformants were screened. 5-10 µL of reaction products was added to 100 µL of DH5a receptor cells followed by incubation on ice for 30 minutes. After being heat shocked in a 42° C. water bath for 50 seconds, the mixture was immediately taken back and incubated in ice for 1 minute. Subsequently, 300-500 μL of LB liquid incubate medium (without antibiotics) was added and cultured in an air bath at 37° C. on a constant temperature shaker at 220 rpm for 1 hour. After that, 200 μL of bacterial solution was sampled from culture and evenly coated onto an agar plate containing 50 μg/ml of antibiotic, then plates were placed in an incubator at 37° C. for overnight cultivation. Universal primers were designed according to the upstream and downstream regions of the recombinant plasmids to perform colony PCR on transformed bacteria. PCR reaction was conducted using the single bacteria colony as the template. PCR products were subsequently detected by agarose gel electrophoresis. Positive clones detected by PCR will be further examined through sequencing.

4. Transforming the recombinant expression vector into an *Escherichia cob* expressing strain, and inducing expression, identification, and purification of the recombinant protein were sequentially conducted. The recombinant plasmid was introduced into *Escherichia coli* BL21 (TransGen Biotech, China), monoclonal clones were select and cultured in LB medium with kanamycin (50 ug/mL) at 220 rpm and 37° C. until the OD600 reached 0.6. IPTG with a final concentration of 0.1 mM (Solarbio, China) was added, and culture was continued for 4-6 hours. Subsequently, culture was centrifuged at 4° C., 6000 rpm, for 10 minutes to collect bacterial precipitates. After adding the sample buffer, precipitate was treated in a boiling water bath for 10 minutes, supernatant was collected after centrifugation and analyzed by 15% SDS-PAGE electrophoresis. The expression of the recombinant protein was preliminary verified using Coomassie blue staining.

The recombinant protein was purified using metal chelation chromatography. By utilizing the chelation properties of imidazole groups on histidine side chains with metal ions ($Ni^{2+}$), the His-tag fusion recombinant protein was purified (GenScript, China). The protein eluted from the nickel column was concentrated through an Amicon Ultra-15 centrifugal filter equipped with Ultracal-30 membrane (Millipore, USA), followed by dialysis (20 mM Tris HCl, 0.15 M sodium chloride, pH 8.0) to remove excess salt and imidazole. The purified protein was obtained by freeze-drying the dialyzed protein, which was further verified by SDS-PAGE electrophoresis, Western blot analysis and Coomassie blue staining combined with mass spectrometry analysis, as shown in FIG. 1. The protein concentration was determined by Bradford method using a kit (Solarbio, China).

Figure 2:
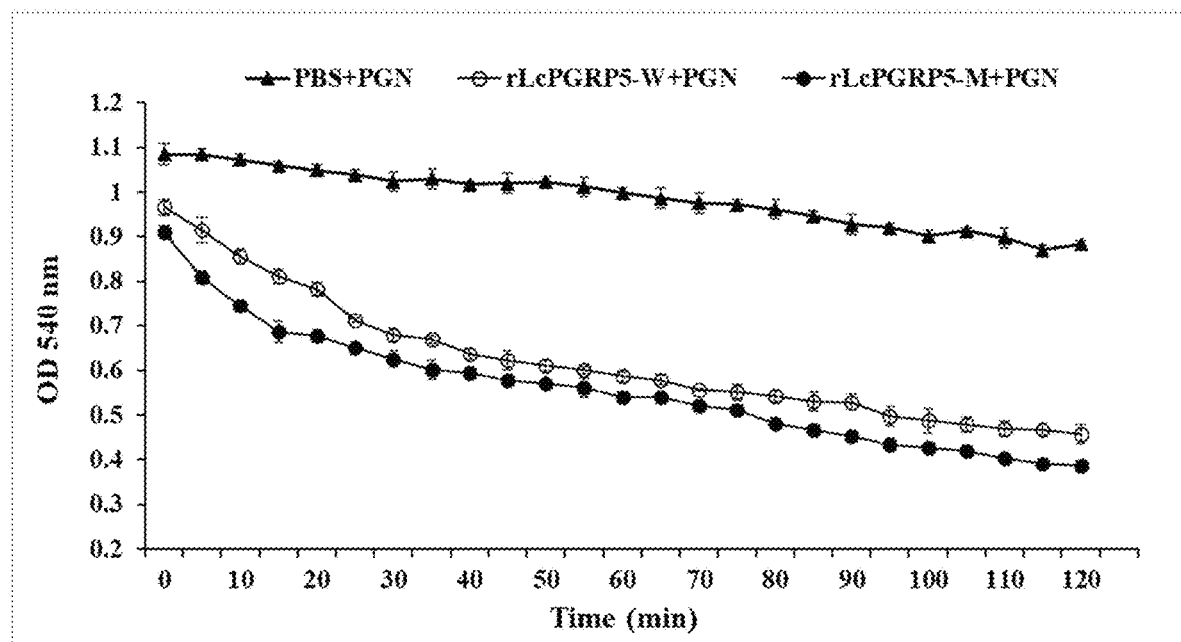
FIG. 2 Amidase activity of the wild (rLcPGRP5-W) and mutant (rLcPGRP5-M) protein in degrading peptidoglycan prepared by the present disclosure.

5. Determination of peptidoglycan recognition protein mutant amidase activity. The amidase activity of wild-type peptidoglycan recognition protein and its mutant protein were detected using UV spectrophotometry. Insoluble peptidoglycan (1 mg/mL, from *Staphylococcus aureus*) with the following solutions were incubated at room temperature: wild-type peptidoglycan recognition protein (0.5 mg/mL) plus Tris-$ZnCl_2$ solution (20 mM Tris-HCl, pH=7.2, 150 mM NaCl, 10 mM $ZnCl_2$), mutant peptidoglycan recognition protein (0.5 mg/mL) plus Tris-$ZnCl_2$ solution, OD540 value was measured and recorded every 5 minutes within 120 minutes. Compared with the wild-type LcPGRP5, the mutant protein exhibited stronger amidase activity, as shown in FIG. 2, which can significantly reduce the OD540 value of PGN solution.

Figure 3:
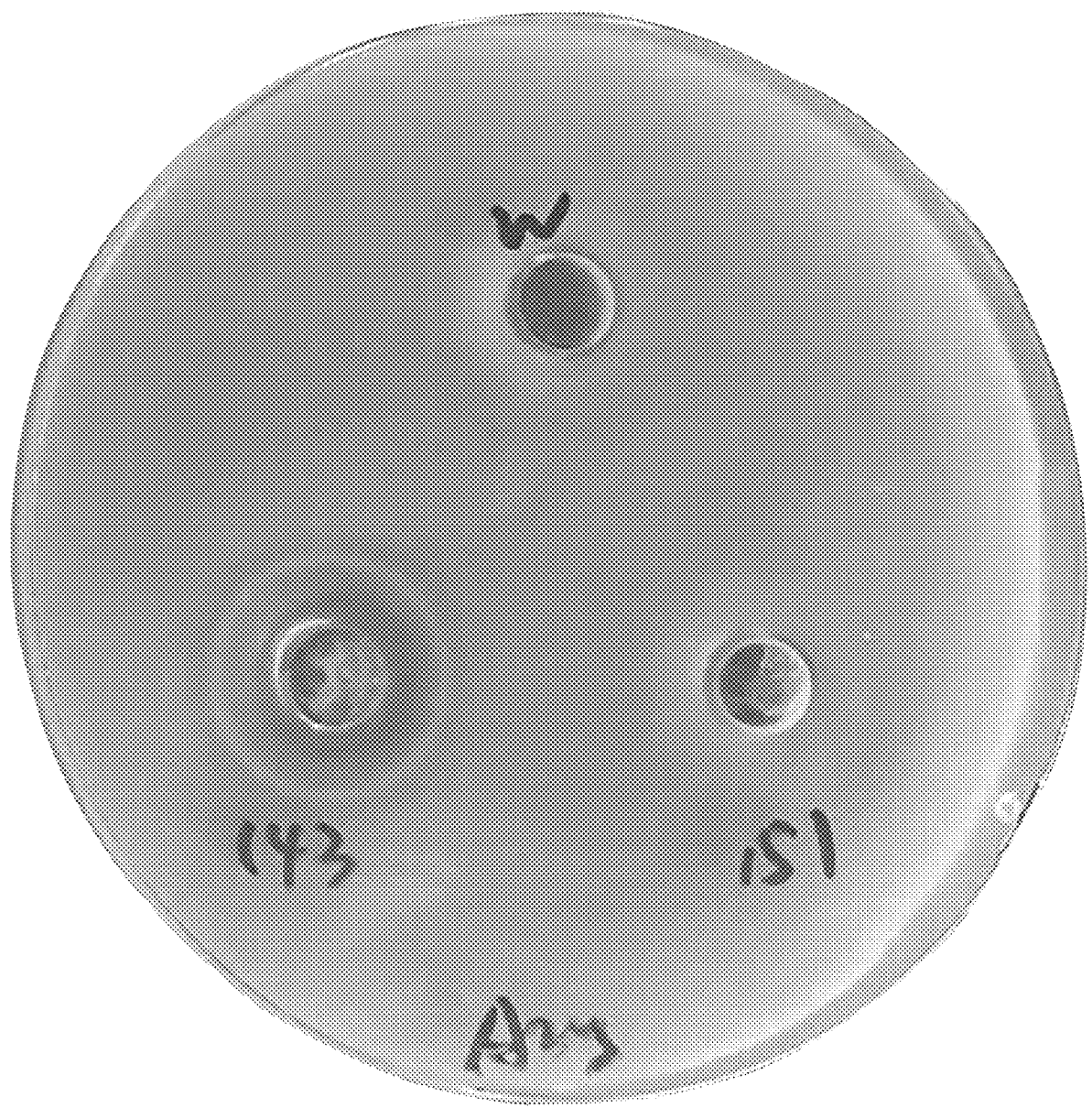
FIG. 3 Antibacterial activity of the wild (W) and mutant protein (143) prepared by the present disclosure.

6. Antibacterial activity assay of n recombinant proteins. The antibacterial activity of recombinant protein was assessed using Oxford Cup method. Under 37° C. cultivation conditions, when *Escherichia coli* and *Staphylococcus aureus* were cultured in LB liquid medium until reaching a logarithmic growth phase, 0.2 mL of bacterial cells were taken and spread evenly onto the surface of agar plate with 2-4 Oxford cups being placed onto each plate. Next, 50-120 μL of recombinant protein was added to each hole. The size of ring-shaped transparent zone after 12 hours of cultivation was measured. Both wild-type and mutant peptidoglycan recognition proteins have inhibitory activity against *Staphylococcus aureus*, the antibacterial activity of mutant recombinant proteins is significantly higher than that of wild-type recombinant proteins, as shown in FIG. 3.

Figure 4:
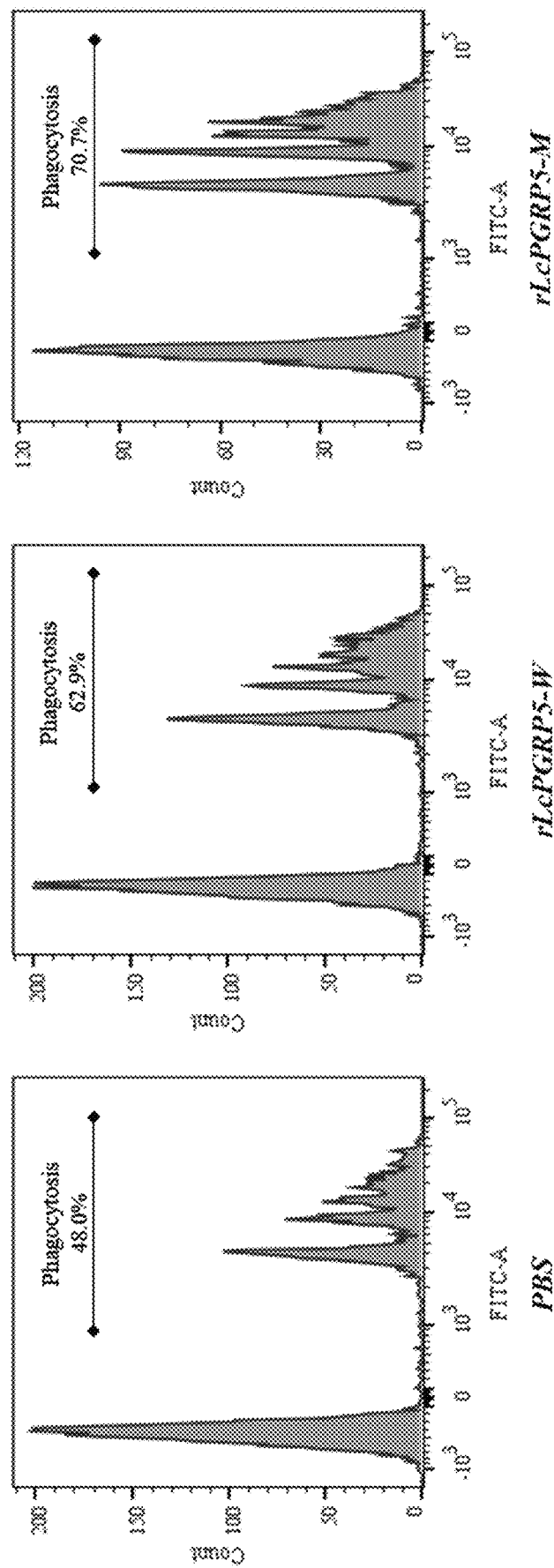
FIG. 4 Phagocytic ability of fish immune cells incubated with the mutant protein prepared by the present disclosure.

7. Effects of LcPGRP5 mutant protein on the phagocytic ability of fish macrophages. Large yellow croaker macrophages were incubated with recombinant proteins to assess the impact on the ability of macrophages to engulf fluorescence-labeled bacteria. To prepare the fluorescently labeled bacteria, D-amino acid conjugated fluorescein (FITC-d-Lys, Bioluminor, Shanghai) was incubated with *Escherichia coli* and *Staphylococcus aureus* in a culture medium for 12 hours. The probe was absorbed by the bacterial body and attached to the bacterial cell wall in covalent bonds. The supernatant was removed by centrifugation, 0.5% formalin was used to kill the bacteria. After centrifugation and washing with PBS three times, a small amount of PBS was added to resuspend the bacteria for use. Large yellow croaker macrophages were incubated with purified recombinant protein (0.1-1 mg/L) for 12-24 hours. Then inactivated *Escherichia coli* or *Staphylococcus aureus* were added and incubated for another 6 hours, pre-cooled culture medium was added to terminate cell phagocytosis, adherent macrophages with trypsin were subjected to a flow cytometry tube, fluorescence (excitation light 488 nm) was record and detected using a flow cytometer (BD, USA). The mutant protein significantly promoted the phagocytic ability of macrophages towards *Staphylococcus aureus*. Specifically, the phagocytic rate of macrophages incubated with recombinant mutant protein showed significantly higher phagocytosis of *Staphylococcus aureus* (70.7%) than that of the treatment group (57.2%) incubated with wild type rLcPGRP5 and control group (48%), as shown in FIG. 4.

What is claimed is:

1. A fish-derived peptidoglycan recognition protein mutant, wherein the amino acid sequence of the mutant is shown in SEQ ID NO. 1, the nucleotide sequence of coding gene of the mutant is shown in SEQ ID NO. 2.

* * * * *